(12) United States Patent
Basheer et al.

(10) Patent No.: US 7,790,429 B2
(45) Date of Patent: Sep. 7, 2010

(54) ROBUST MULTI-ENZYME PREPARATION FOR THE SYNTHESIS OF FATTY ACID ALKYL ESTERS

(75) Inventors: Sobhi Basheer, Sakhnin (IL); Maisa Haj, Shfar-Am (IL); Muhammad Kaiyal, Maker (IL)

(73) Assignee: Transbiodiesel Ltd., Haifa (IL)

( * ) Notice: Subject to any disclaimer, the term of this patent is extended or adjusted under 35 U.S.C. 154(b) by 71 days.

(21) Appl. No.: 11/946,121

(22) Filed: Nov. 28, 2007

(65) Prior Publication Data

US 2009/0133322 A1    May 28, 2009

(51) Int. Cl.
    C12N 9/20         (2006.01)
(52) U.S. Cl. ........................................ 435/198; 435/134
(58) Field of Classification Search ................. 435/134, 435/198
    See application file for complete search history.

(56) References Cited

U.S. PATENT DOCUMENTS

2003/0175918 A1*  9/2003  Basheer ..................... 435/176

FOREIGN PATENT DOCUMENTS

| EP | 1705238 A1 | 9/2006 |
| KR | 673837 B1 | 11/2005 |
| WO | 2008/084470 | 7/2007 |

OTHER PUBLICATIONS

Lee et al., Biotech. and Bioprocess, vol. 11, pp. 522-525.*
Lee et al: "Optimization of the process for biodiesel production using a mixture of immobilized *Rhizopus oryzae* and *Candida rugosa* lipases" Journal of Microbiology and Biotechnology, vol. 18, Jul. 29, 2008, pp. 1927-1931.*
Biodiesel Production Using a Mixture of Immobilized *Rhizopus oryzae* and *Candida rugosa* Lipases, Biotechnology and Bioprocess Engineering 2006, 11:522-525.
Lee D. H. et al. (2006) Lipase Immobilization on silica gel using a cross-linking method, J. Ind. Eng. Chem., 12 (5):577-782.
Lee D. H. et al. (2006) Pretreatment of lipase with soybean oil before immobilization to prevent loss of activity, Biotechnol. Lett. 28: 1965-1969.
Y. Watanabi et al., J. Am. Oil Chem. Soc. 84 (2007), 1015-1021.
E. Hernandez-Martin, C. Otero, Bioresource Technology, 99 (2008), 277-286.

(Continued)

*Primary Examiner*—Deborah D Carr
(74) *Attorney, Agent, or Firm*—Roach Brown McCarthy & Gruber, P.C.; Kevin D. McCarthy (57) ABSTRACT

A process for the preparation of short-chain alkyl esters of fatty acids, preferably fatty acid methyl esters (biodiesel) in solvent-free system is disclosed. In particular, the process comprises (a) providing a fatty acid source, (b) stepwise adding a short-chain free alcohol, preferably methanol, or any other alcohol donor, to said fatty acid source in the presence of a lipase preparation and (c) allowing the reaction to proceed under suitable conditions, until said fatty acid source triglycerides are converted to fatty acid methyl esters (FAME). The lipase preparation comprises at least two lipases. The two lipases being separately or jointly immobilized on a suitable support and wherein at least one of the lipases has increased affinity for partial glycerides and at least one of the lipases is sn-1,3 positional specific.

32 Claims, 4 Drawing Sheets

OTHER PUBLICATIONS

Y. Watanabi et al., J. Molecular Cat. B: Enzymatic 44 (2007), 99-105.

L. Fjerbaek, et al., Biotechnol. Bioeng. 102(5) (2009), 1298-1315.

H. Noureddini, et al., Bioresource Technology 96 (2006), 769-777.

International Search Report for PCT/IL2008/001497 - 3 pages - mailed Jun. 16, 2009.

Kim et al., "Optimization for biodiesel production using a mixture of immobilized *Rhizopus oryzae* and *Candida rugosa* lipases," J. of Biotechnology, v. 131, n. 2, Sep. 2007, p. S123 - 1 page.

Li et al., "Lipase-catalyzed transesterification of rapeseed oils for biodiesel production with a novel organic solvent as the reaction medium" J. Molecular Catalysis B: Enzymatic, v. 43, 2006, pp. 58-62, section 4.3 and the conclusion, - 6 pages.

Ranganathan et al., "An overview of enzymatic production of biodiesel," Bioresource Technology, v. 99, Jun. 25, 2007, pp. 3975-3981 - 8 pages.

Soumanou et al., "Improvement in lipase-catalyzed synthesis of fatty acid methyl esters from sunflower oil." Enzyme and microbial technology, v. 33, 2003, pp. 97-103 - 8 pages.

Lee et al., "Optimization for biodiesel production using a mixture of immobilized *Rhizopus oryzae* and *Candida rugosa* lipases," J. of Microbiology and Biotechnology, v. 18, Jul. 29, 2008- pp. 1927-1931 - 6 pages.

Basheet et al., "99th AOCS Annual meeting and Expo/ New Immobilized lipases for production of biodiesel" May 2008, pp. 1-5 - 6 pages.

Salis et al., "Role of the support surface on the loading and the activity of Pseudomonas fluorescens lipase used for biodiesel synthesis." J. Molecular Catalysis B: Enzymatic, v. 57, Oct. 10, 2008 - pp. 262-269 - 8 pages.

\* cited by examiner

ROBUST MULTI-ENZYME PREPARATION FOR THE SYNTHESIS OF FATTY ACID ALKYL ESTERS

FIELD OF THE INVENTION

The invention relates to the preparation of an immobilized multi-enzyme system for transesterification or esterification of oils and fats triglycerides or fatty acids with short-chain alcohols, to obtain fatty acid short-chain alkyl esters, preferably to be used as biodiesel. The invention also relates to a process for the preparation of such multi-enzyme immobilized systems, and their various industrial uses in one-step or in multi-step process, particularly for the production of methyl esters, typically used as biodiesel, at approximately complete conversions.

BACKGROUND OF THE INVENTION

Lipases (triacylglycerol hydrolase E.C. 3.1.1.3) are defined as hydrolytic enzymes that act on the ester linkage in triacylglycerol in aqueous systems to yield free fatty acids, partial glycerides and glycerol. This group of enzymes under low water activity is capable of catalyzing their reverse hydrolysis reaction. The reverse catalytic activity of lipases has been widely exploited for the synthesis of valuable compounds that contain ester and amide linkages or other related chemicals containing functional groups such as hydroxyl, carboxylic and amino groups. In particularly, lipases have been utilized for reforming fats, oils, waxes, phospholipids and sphingolipids to obtain new desired functional properties, and for separating optically active compounds from their racemic mixtures. Of particular interest, the use of a multi-enzyme system comprised of different lipases immobilized on a polymeric support will be disclosed for the synthesis of fatty acid short-chain alkyl esters (biodiesel).

Currently, there are more than 40 different lipases and phospholipases commercially available however only a few of them are prepared in commercial quantities. Some of the most industrially promising interfacial enzymes are derived from *Candida antarctica, Candida rugosa, Rhizomucor miehei, Pseudomonas* sp., *Rhizopus niveus, Mucor javanicus, Rhizopus oryzae, Aspergillus niger, Penicillium camembertii, Alcaligenes* sp., *Burkholderia* sp., *Thermomyces lanuginosa, Chromobacterium viscosum*, papaya seeds, and pancreatin.

The most familiar enzyme immobilization techniques are in general divided according to the following:
1. Physical adsorption of enzymes to solid supports, such as silica and insoluble polymers.
2. Adsorption on ion-exchange resins.
3. Covalent binding of enzymes to a solid support material, such as epoxidated inorganic or polymer supports.
4. Entrapment of enzymes in a growing polymer.
5. Confinement of enzymes in a membrane reactor or in semi-permeable gels.
6. Cross-linking enzyme crystals (CLECS's) or aggregates (CLEAS's).

Physical adsorption of lipases based on use of polymeric supports with high porosity or use of ion-exchange resins are the most practiced immobilization methods for lipases. This method is characterized with its simplicity and yielding reliable synthetic activity.

The use of free or immobilized lipases for transesterification of triglycerides and short-chain alcohols to form fatty acid alkyl esters has yielded unsatisfactory results with respect to activity and stability of the enzyme. Also, the cost-effectiveness of the immobilized enzymes, for carrying out enzymatic production of fatty acid alkyl esters at industrial quantities, is still prohibited. Furthermore, it has been reported that all currently available lipases in either their free or immobilized forms are incapable of reaching near to complete conversions, preferably above 99%, for oil triglycerides to fatty acid alkyl esters at reasonable reaction time, particularly below 8 hours.

Another major drawback of lipases results from their low tolerance towards hydrophilic substrates, particularly short-chain alcohols, short-chain fatty acids (both below C4), water and glycerol typically present in the transesterification reaction medium. It has been observed in many research studies that short-chain alcohols and short-chain fatty acids, such as methanol and acetic acid, respectively, are responsible for detaching essential water molecules from the quaternary structure of those enzymes, leading to their denaturation and consequently loss of their catalytic activity. Also, the presence of such hydrophilic molecules in the reaction medium, results in detaching the enzyme molecules from the support and consequently decrease in the enzyme operational lifetime. Therefore, it is not surprising that the application of lipases for production of commercial quantities of fatty acids methyl esters "biodiesel" using oil triglycerides and methanol as substrates is infeasible.

Use of mixtures of lipases has been suggested [Lee, D. H. et al., Biotechnology and Bioprocess Engineering 2006, 11:522-525]. This publication describes production of biodiesel using a mixture of chemically bound, immobilized *Rhizopus oryzae* and *Candida rugosa* lipases. As can be seen, the reaction time was relatively long, typically more than 24 hours to reach conversions over 96% to biodiesel. Also, the results presented in this publication show that the mixture of enzymes used lost more than 20% of its initial activity after as few as 10 cycles of use. This may be attributed to the accumulation of partial glycerides intermediates in the reaction system, which decrease the transesterification reaction and thus prolong the reaction time. The deactivation of the biocatalyst in the system described in this publication is a key drawback, which prevents its industrial application.

It is therefore an object of this invention to provide a new method for obtaining highly active and stable immobilized lipases for the synthesis of fatty acids alkyl esters, especially fatty acid methyl esters for use as "biodiesel".

It is a further object of the present invention to provide highly active, and stable, immobilized multi-enzyme preparation which possesses high tolerance towards short-chain alcohols and short-chain fatty acids, especially methanol, ethanol and acetic acid respectively, and other polyols such as glycerol, as well as other inhibiting factors typically present in oils and fats, in particularly of inedible grade.

It is a further object of the present invention to provide a one-step or multi-step enzyme reactor configuration for obtaining the desired product, namely, fatty acid alkyl esters at near to complete conversions during reasonable reaction time, typically below 5 hours.

SUMMARY OF THE INVENTION

In a first aspect, the invention relates to a process for the preparation of a mixture of lipases immobilized on an insoluble support, said mixture preferably comprising a lipase having sn-1,3 positional specificity and a lipase having increased affinity for mono- and diglycerides, the process comprising the steps of contacting a buffer solution containing a sn-1,3-specific lipase with a polymeric matrix, preferably an ion exchange resin or an adsorbent; preferably, in the presence of a hydrophobic organic solvent, such as n-hexane, added to the immobilization medium at ratios of 1:10 to 10:1 buffer:organic solvent, respectively; mixing the system so obtained for at least 4 hours at room temperature; and filtering off of the immobilized lipase mixture, and drying it, for example over silica, or by other means, to a water content of less than 5%.

The sn-1,3 positional specific lipase may be, but is not limited to *Thermomyces lanuginose, Rhizomucor miehei, Mucor miehei, Pseudomonas* sp., *Rhizopus* sp., *Mucor javanicus, Penicillium roqueforti, Aspergillus niger, Acromobacter* sp. or *Burkholderia* sp. The lipase having increased affinity for partial glycerides may be, but is not limited to *Candida antarctica* B, *Candida rugosa, Alcaligenes* sp. or *Penicillium camembertii*. Other lipases contemplated within the scope of this application may be *Rhizopus niveus, Rhizopus oryzae, Burkholderia* sp., *Chromo-bacterium viscosum*, papaya seeds or pancreatin.

The immobilization of the different lipases can be carried out either in one pot or separately.

The insoluble support is capable of binding lipases by physical adsorption or by covalent binding to its functional groups. The support is preferably a porous support which may be organic or inorganic, preferably selected from the group consisting of porous inorganic support such as silica- or alumina-based supports, organic supports such as polymer-based supports, wherein said support may optionally contain active functional groups such as epoxy or aldehyde groups, or ionic groups.

Specific non-limiting examples of suitable supports are an Amberlite XAD, such XAD 4, XAD 16, XAD-1600, XAD 7HP, XAD 16HP, XAD 1180, Amberlite FPA53, Amberlite FPC22H, Amberlite FPA40Cl, Amberlite IRC50, a Duolite, such as A&, A561, A568 and Duolite C467, Aberlyst A-21, Dowex Monosphere 77, Dowex Optipore L493, Dow Styrene DVB, MTO Dowex Optipore SD-2, Dowex MAC-3, Purolire A109, and Sepabeads such as EC-EA, EC-EP, EC-BU and EC-OD.

In a further embodiment, the invention relates to an enzymatic process for the preparation of fatty acid alkyl esters at conversions above 98% comprising the step of reacting a fatty acid source, such as free fatty acid, triglyceride, fatty acid esters, partial glycerides, phospholipids or other fatty acid derivatives with an alcohol, such as methanol, or any other alcohol donor, in the presence of a lipase preparation and allowing the reaction to proceed under suitable conditions, until said fatty acid source triglycerides are converted to fatty acid methyl esters (FAME), wherein said lipase preparation comprises at least two lipases, said lipases being separately or jointly immobilized on a suitable support and wherein at least one of said lipases has increased affinity for partial glycerides and at least one of said lipases is sn-1,3 positional specific. The lipase preparation may be prepared by the process of the invention.

The fatty acid source may comprise at least one of soybean oil, canola oil, rapeseed oil, olive oil, castor oil, palm oil, sunflower oil, peanut oil, cotton seed oil, Jatropha oil, animal-derived fat, waste cooking oil, oil triglycerides derived from inedible plant sources, or any mixture of at least two thereof.

The lipases may be jointly immobilized on a suitable support. Alternatively, each of the lipases may be immobilized on a suitable support, with the supports on which the said lipases are immobilized being identical or different.

The conversion of the fatty acid acyl groups or free fatty acids comprised in said fatty acid source to fatty acid methyl esters is monitored at various time points during the reaction, the reaction medium and optionally intermediates are removed by suitable means at any desired time point during the reaction, which removal stops the reaction, and the formed fatty acid methyl esters and optionally the formed glycerol are isolated from the reaction medium. The reaction is preferably stopped when the conversion of the fatty acid acyl groups or free fatty acids comprised in said fatty acid source to fatty acid methyl esters has reached at least 70%, preferably at least 85%, more preferably at least 95%.

The invention further relates to a solvent-free process for the preparation of short-chain alkyl esters of fatty acids, preferably fatty acid methyl esters (biodiesel) which process comprises providing a fatty acid source, stepwise adding a short-chain free alcohol, preferably methanol, or any other alcohol donor, to said fatty acid source in the presence of a lipase preparation and allowing the reaction to proceed under suitable conditions, until the conversion of the fatty acid acyl groups or free fatty acids comprised in said fatty acid source to fatty acid methyl esters reaches at least 70% wherein the lipase preparation comprises a single one lipase immobilized on a suitable support, or a mixture of at least two lipases jointly or separately immobilized on a suitable support, while continuously removing the formed glycerol and any excess water from the reaction mixture. In this process, the lipase preparation comprises at least two lipases, said lipases being separately or jointly immobilized on a suitable identical or different supports. At least one of the lipases has increased affinity for partial glycerides and at least one of said lipases is sn-1,3 positional specific. The lipases, supports and fatty acyl sources are as described above.

Also in this embodiment, the conversion of the fatty acid acyl groups or free fatty acids comprised in said fatty acid source to fatty acid methyl esters is monitored at various time points during the reaction, the reaction medium and optionally undesired intermediates are removed by suitable means at any desired time point during the reaction, thereby stopping the reaction, and the formed fatty acid methyl esters and optionally the formed glycerol are isolated from the reaction medium. The reaction may be stopped when the conversion of the fatty acid acyl groups or free fatty acids comprised in said fatty acid source to fatty acid methyl esters has reached at least 70%, preferably at least 85%, more preferably at least 95%.

The reaction mixture contained in a thermostated reactor bottomed with a filter is reacted under suitable conditions, until said fatty acyl groups or fatty acids are converted to fatty acid methyl esters. The reaction medium is filtered through the bottom filter by gravitational force or by applying nitrogen pressure on top of the reactor.

In order to reach conversions higher than 98% at reasonable reaction time, preferably less than 4 hours, the reaction cab be carried out at two stages. First, the source of fatty acids is reacted with short-chain alcohol, such as methanol, for approximately 2 hours where conversions to fatty acid alkyl esters above 70% are obtained. The reaction medium is removed from the reactor bottom maintaining the biocatalyst in the reactor. The reaction medium is allowed to separate into phases or centrifuged in order to remove the formed glycerol. Then, the upper organic phase containing mainly the residual unreacted glycerides and the formed fatty acid alkyl esters is introduced to a second consecutive reactor and allowed to react with methanol in the presence of a lipase or multi-lipase immobilized on a polymeric matrix.

This process yields fatty acid alkyl esters of content higher than 98% and a by-product, namely glycerol, of high quality. The prepared multi-enzyme immobilized preparation is recyclable with insignificant activity losses after reuse in more than 100 cycles.

Still further, the invention relates to a solvent-free process for the preparation of short-chain free alkyl esters of fatty acids, preferably fatty acid methyl esters (biodiesel) which process comprises a first step of providing a fatty acid source, stepwise adding a short-chain alcohol, preferably methanol, or any other alcohol donor, to said fatty acid source in the presence of a lipase preparation and allowing the reaction to proceed under suitable conditions, until the conversion of the fatty acid acyl groups or free fatty acids comprised in said fatty acid source to fatty acid methyl esters reaches at least 70% wherein said lipase preparation comprises at least one lipase immobilized on a suitable support, or a mixture of at least two lipases jointly or separately immobilized on a suitable support, while continuously removing the formed glycerol from the reaction mixture, to yield an organic phase containing mainly residual un-reacted glycerides and the formed fatty acid alkyl esters; and reacting the said organic phase with a short-chain free alcohol, preferably methanol, or any other alcohol donor, in the presence of a lipase preparation as defined for the first step under suitable conditions, until the conversion of the fatty acid acyl groups or free fatty acids comprised in said fatty acid source to fatty acid methyl esters reaches at least 95%.

Also in this embodiment, the lipase preparation comprises at least two lipases, being separately or jointly immobilized on a suitable identical or different supports. At least one of the lipases has increased affinity for partial glycerides and at least one of said lipases is sn-1,3 positional specific.

In this process, the support, the lipases and the fatty acid source are as described and defined above.

The invention will be described in more detailed on hand of the attached drawings.

DETAILED DESCRIPTION OF THE INVENTION

In order to improve and facilitate the enzymatic production of bio-diesel, the present invention is primarily aimed at preventing enzyme deactivation which commonly results from exposure either to methanol, which is one of the starting materials, or from exposure to the glycerol formed in the process. The Novozyme 435 lipase (*Candida antarctica* lipase B), immobilized on an adsorbent, which has been used in the past, is characterized with loss of activity after as few as 10 reaction cycles in average, due to the above deactivation. The present invention aims at solving this problem.

Furthermore, in order to reach conversions higher than 96%, the transesterification reaction time of oils and methanol is relatively long, typically in the range of 24-48 hours, with said Novozyme 435 as well as other lipases. It is also an object of the invention to provide a process and enzyme preparations which would considerably shorten the reaction time.

In addition, the glycerol by-product formed in the process leads to enzyme deactivation because it is maintained on the biocatalyst particles. The adherence of glycerol on biocatalysts leads to lowering or to somehow total loss of the enzyme activity. The process and preparations of the invention are also aimed at solving this problem.

Further, prior art works used lipases which led to the formation and accumulation of partial glycerides, including mono- and diglycerides, in the reaction system. Low reaction rates for transesterification of such lipases for those substrates resulted in prolonging the reaction time needed for reaching conversions higher than 96%. The present invention provides for enzymatic preparations, system and process which facilitate a high rate clearance for the intermediates formed in the course of the enzymatic transesterification, and therefore reach high conversions in short reaction times.

More specifically, the invention provides for the use of multi-enzyme system in one- or two-step processes, which overcomes the above obstacles, giving unexpected results, and exhibiting synergy between the immobilized enzymes and avoidance of enzyme deactivation, and also because of efficient combinations of both lipase-lipase and lipase-matrix.

The present inventor has thus developed highly active and stable immobilized enzyme preparations, having high tolerance towards hydrophilic substrates, such as short-chain alcohols and short-chain fatty acids, for improving enzymatic processes for the production of fatty acid alkyl esters, specifically fatty acid methyl esters "bio-diesel".

In a first embodiment, the developed biocatalyst is comprised of a mixture of lipases of different types, immobilized on a polymeric matrix. In accordance with the invention, different lipases may be immobilized in the same reaction pot or separately, on same or different supports. Optionally, different lipases can be immobilized separately on different supports, depending on the best combination enzyme-support with regard to resistance to short-chain alcohols, esterification/transesterification activity and operational life-time for the biocatalyst. The lipase mixture in accordance with the invention comprises a lipase which is sn-1,3 positional specific with a random lipase, specifically lipase that has affinity to partial glycerides.

In a further aspect, the invention provides a process for the preparation of bio-diesel, which is characterized by continuous removal of all or some of the reaction products and/or by-products. The disclosed enzymatic process can be carried out either in one stage or in two stages, in order to reach conversion of the raw materials to their corresponding fatty acid alkyl esters higher than 98%. The novel process of the invention can employ the lipase preparation in accordance with the invention, or a single lipase immobilized on a solid support. In such case, the lipase can be random or 1,3-specific, and the combination lipase/support is designed with care, to give a robust and efficient enzyme preparation.

In order to reach conversions of raw materials to above 98% two types of process configurations were used:
1. Stirred tank reactor with a bottom sintered glass filter which retains the biocatalyst in the reactor, however allows the reaction medium to permeate through out of the reactor. Such reactor configuration allows the by-product, specifically glycerol, to sink to the bottom of the reactor, and permeate out through the sintered glass filter. The result is continuous removal of the formed glycerol and also of excess water, out of the reaction medium, leading to shift of the reaction towards synthesis, thereby reaching conversions above 98%. The biocatalyst used in this reactor may be comprised of a single or multi-types of lipases, in consideration of their positional specificity as well as their origin.
2. Two consecutive stirred tank reactors with a bottom sintered glass filter. A settling tank or centrifuge is used between the two reactors. The first reactor may contain an immobilized biocatalyst comprised of a single or multi-types of lipases. The role of the settling tank or centrifuge between both reactors is to remove the formed glycerol and excess water from the reaction medium, leading to an increase in the conversion of the raw materials to their corresponding fatty acid alkyl esters to above 98% in the second reactor at reasonable reaction time.

In the process of the invention, there is no accumulation of partial glycerides in the system which are typically responsible for loss of enzyme activity together with accumulated glycerol. As will be shown in the following Examples, in the process of the invention the biocatalyst activity is unexpectedly retained in repeated use of same enzyme preparation over more than 100 cycles. The reaction time is shortened to less than 4 hours, in comparison to more than 24 hours when other biocatalysts as described in prior art are used in order to reach conversions higher than 96%. These features impart the enzyme preparations and process of the invention with high economic value.

The solid support on which the lipase/s is/are immobilized is preferably a porous support which may be organic or inorganic, particularly selected from the group consisting of porous inorganic supports such as silica- or alumina-based supports, organic supports such as polymer-based support, wherein said support may optionally contain active functional groups such as epoxy or aldehyde groups, or ionic groups. Some specific supports are given in the Examples below, particularly in Table 1.

Preferably, a hydrophobic organic solvent, such as n-hexane, can be added to the immobilization medium at ratios of 1:10 to 10:1 buffer:organic solvent, respectively. The immobilized enzymes of the invention prepared by the method of the invention are very active and particularly stable and of high tolerance to hydrophilic substrates, such as short-chain alcohols, short-chain fatty acids and other deactivating enzyme factors typically present in waste oil. Conversions of the fatty acid source of about 90% in the first stage and higher than 98% in the second stage, are retained after even 100 cycles of reaction. This stability is of major economic importance.

Immobilization can be effected in accordance with procedures described in the art. A specific advantageous method of immobilization is described in applicant's co-pending Israel Patent Application No. 180598, filed on Jan. 8, 2007, fully incorporated herein by reference. Briefly, the preparation of a lipase immobilized on an insoluble support, is effected by providing a bi-phase system comprised of an aqueous buffer solution and at least one first organic solvent; mixing said interfacial enzyme with the bi-phase system; adding the support to the obtained mixture and mixing; and isolating from the obtained mixture the interfacial enzyme immobilized on said support.

The choice of enzyme is of importance for the efficiency of the enzyme preparation of the invention, particularly for the multi-lipase systems. The combination should be chosen such that deactivation in the harsh conditions of the reaction is avoided. This can be fulfilled only because of both enzymes in the system work synergistically. It is to be understood, that by the term synergism as used herein is also meant the avoidance of enzyme deactivation. For example, without being bound by theory, some of the transesterification intermediates, mainly monoglycerides and diglycerides, appear to be responsible for the deactivation of lipase derived from *Pseudomonas* sp. (herein SP), and lipase derived from *Thermomyces lanuginose* (herein TL). On the other hand lipase derived from *Candida Antarctica* B (herein CALB), has high specificity towards monoglycerides and diglycerides. The presence of CALB and either PS or TL guarantees synergistic effects as defined herein, and thus maintaining the complex biocatalyst with no significant activity loss in repeated use. Specific combinations of enzymes, and rationale underlying their design will be described in more detail in the following examples. The main point in lipase immobilization within the context of this application is to find the most appropriate matrix to fit the enzyme proteins. This is because possessing high transesterification activity for a specific combination of lipase-matrix does not guarantee the maintenance of the activity in repeated use. The present inventor has established particularly efficient combinations, such as, but not limited to those described herein.

The use of a two-lipase system in accordance with the invention, which possesses high transesterification activity of methanol and oils, and also high stability under the extreme reaction conditions, imparts the developed biocatalyst economic value in the production of bio-diesel, with minor costs of the biocatalyst, which can be most efficiently reused.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the intended scope of the invention.

EXAMPLES

Example 1

Preparation of a Single Lipase Immobilized on a Polymeric Support

Lipase derived from *Thermomyces lanuginosa* (1 ml of Lipozyme TL 100L), or a lipase concentrate derived from *Thermomyces lanuginose*, (Novozymes, Denmark) was solubilized in a TRIS buffer solution (12 ml) of 0.05M and pH 8. The lipase solution was contacted with an enzyme support (1 g, the various supports used are shown in Table 1 below) by shaking or stirring for 8 hours at room temperature. Preferably, a hydrophobic organic solvent, such as n-hexane is added to the immobilization medium at ratios of 1:10-10:1 buffer:organic solvent, respectively. The support containing the immobilized enzyme was filtered off and dried in a desiccator overnight to yield the immobilized lipase. The same procedure was repeated, using either lipase derived from *Pseudomonas* sp. (100 mg Lipase PS, Amano Enzyme, Japan), lipase derived from *Alcaligenes* sp., (50 mg lipase QLM, Meito Sangyo, Japan) or *Candida antarctica* B lipase concentrate (1 ml, CALB-L, Novozymes, Denmark). These immobilized lipases can be used either separately, in the novel process of the invention, or in combination at different weight ratios in one-pot reaction system or in consecutive two-step or more processes for the preparation of fatty acid alkyl esters (biodiesel) via esterification/transesterification reactions of fatty acid source and alcohol, typically methanol for biodiesel.

Example 2

Preparation of Multi-lipase Immobilized Biocatalysts

Lipase derived from *Thermomyces lanuginosa* (1 ml of Lipozyme TL 100L, Novozymes, Denmark) and *Candida antarctica* B lipase concentrate (1 ml, CALB-L, Novozymes, Denmark) were solubilized in a buffer solution (12 ml) of 0.05M and pH 8. The solution containing both enzymes was contacted with a support, such as Amberlite XAD 7HP (1 g) by shaking or stirring for 8 hours at room temperature. Preferably, a hydrophobic organic solvent, such as n-hexane, is added to the immobilization medium at ratios of 1:10-10:1 buffer:organic solvent, respectively. The support containing the immobilized enzymes was filtered off and dried in a desiccator overnight to yield immobilized multi-lipase preparation. The same procedure was repeated, using a solution containing either both lipase PS (100 mg, Amano Enzyme, Japan) and *Candida antarctica* B lipase concentrate (1 ml, CALB-L, Novozymes, Denmark), lipase PS (100 mg, Amano Enzyme, Japan) and *Thermomyces lanuginosa* lipase concentrate (1 ml, CALB-L, Novozymes, Denmark). Other multi-enzyme systems can be prepared, such as, for example, using lipase derived from *Alcaligenes* sp. (50 mg, lipase QLM, Meito-Sangyo, Japan) in combination with either lipase PS or lipase TL.

Example 3

Preparation of Fatty Acid Methyl Esters (FAME, Biodiesel) using Immobilized Lipases Table 1 shows the percentage of the formed fatty acid methyl esters (FAME %) in transesterification reaction using lipases derived from *Thermomyces lanuginose* (TL), *Pseudomonas* sp. (PS) and *Candida antarctica* B (CALB), which were each immobilized separately on different supports. Reactions were carried out by adding immobilized lipase (30 g) to soybean oil (220 g) and methyl alcohol (23.9 g) (a stoichiometric ratio of 1:3 between oil triglycerides and methanol, respectively) into a double-jacketed glass reactor bottomed with a sintered glass filter of porosity of 70-100 μm. The methanol was added in batches each batch is ⅓ of the stoichiometric amount or titrated drop-wise. The reaction system is mechanically stirred at 30° C. Progress of the conversion of the raw materials is determined by measuring the percentage of fatty acid methyl esters, partial glycerides and triglycerides using GC after 8 hours of reaction time under the above mentioned conditions.

Results are given in Table 1, which shows the percentage of the formed fatty acid methyl esters in transesterification system comprised of soybean oil triglycerides (220 g) and methanol (23.9 g) using different, individually immobilized lipases prepared according to Example 1 (30 g). The reaction mixture was mechanically stirred at 30° C. for 8 hours.

TABLE 1

| Immobilized lipase/<br>Type of support | *Thermomyces lanuginosa* lipase | *Pseudomonas* sp. lipase FAME (%) | *Candida antarctica* lipase FAME (%) |
|---|---|---|---|
| Amberlite XAD 4 | 45 | 55 | 20 |
| Amberlite XAD 16 | 47 | 85 | 55 |
| Amberlite XAD 7HP | 55 | 86 | 40 |
| Amberlite XAD 16HP | 46 | 80 | 40 |
| Duolite XAD 761 | 50 | 85 | 40 |
| Amberlite XAD 1180 | 55 | 87 | 70 |
| Amberlite XAD 1600 | 60 | 80 | 70 |
| Duolite A7 | 65 | 85 | 40 |
| Duolite A561 | 65 | 85 | 75 |
| Duolite A568 | 54 | 80 | 40 |
| Duolite C467 | 75 | 10 | 0 |
| Amberlyst A-21 | 55 | 80 | 40 |
| Dowex monosphere 77 | 40 | 80 | 40 |
| Dowex optipore L493 | 10 | 55 | 0 |
| Dow styrene DVB | 5 | 35 | 5 |
| MTO Dowex optipore SD-2 | 5 | 75 | 5 |
| Dowex MAC-3 | 0 | 0 | 0 |
| Amberlite FPA53 | 45 | 70 | 35 |
| Amberlite FPC22H | 0 | 0 | 0 |
| Amberlite FPA4OCl | 45 | 47 | 45 |
| AmberliteIRC50 | 5 | 15 | 45 |
| Purolire A109 | 45 | 75 | 45 |
| Sepabeads EC-EA | 75 | 85 | 70 |
| Sepabeads EC-EP | 80 | 85 | 75 |
| Sepabeads EC-BU | 85 | 86 | 85 |
| Sepabeads EC-OD | 80 | 85 | 85 |

Example 4

Synthesis of Fatty Acid Methyl Esters (Biodiesel) Using Immobilized Multi-lipase Preparation Table 2 shows the percentage of the formed fatty acid methyl esters (FAME %) in transesterification reaction using multi-lipase preparation immobilized on Amberlite XAD 7HP comprised of either *Thermomyces lanuginose* (TL) lipase and *Candida antarctica* lipase B (CALB), or *Pseudomonas* sp. (PS) lipase and *Candida antarctica* lipase B, which were immobilized separately, or together on the same support in one-pot system. Also, instead of CALB, a lipase derived from *Alcaligenes.* sp. (Lipase QLM, Meito-Sangyo, Japan) was used in combination with lipases PS or TL. Reactions were carried out by adding immobilized lipase preparation (30 g) to soybean oil (220 g) and methyl alcohol (23.9 g) into a double-jacketed glass reactor bottomed with a sintered glass filter of porosity of 70-100 µm. The methanol was added in batches, each batch being ⅓ of the stoichiometric amount or titrated drop-wise. The reaction system is mechanically stirred at 30° C. Progress of the conversion of the raw materials is determined by measuring the percentage of fatty acid methyl esters, partial glycerides and triglycerides using gas chromatography (GC) after 2, 3 and 6 hours of reaction time under the above mentioned conditions.

The results presented in Table 2 show that lipases TL and PS could not reach FAME at concentration of above 95% after 6 hours of reaction time, while transesterification activity of CALB was relatively slow. A multi-lipase immobilized preparation comprised of lipases TL and CALB surprisingly exhibited lower transesterification activity than the control experiment with lipase TL. Without being bound by theory, this can be attributed to the TL lipase being responsible for decreasing the reaction rates as it catalyzes the reaction between the formed glycerol and FAME to yield glycerides.

This example demonstrates the advantage in using of a two-step reaction system, where in the first step the reaction medium is subjected to lipase TL, which favors triglycerides as substrates, reaching conversions above 70% in 2 hours, and then the formed glycerol is removed. In the second step, where the concentrations of the intermediate products, specifically mono- and diglycerides are relatively high, these intermediates can be favorably transesterified by CALB. Thus, when a single-enzyme system is used in the first reaction step, the biocatalyst used in the second step which comprises a lipase that has high affinity for mono- and diglycerides, such as CALB, together with at least one other enzyme with high substrate specificity to triglycerides, such as lipases PS, TL and QLM, will complete the reaction. Thus, when in the first step only lipase TL is used, a mixture of lipase TL and CALB is used in the second step, or when lipase PS and CALB are used in the first step, lipase PS and CALB are used in the second step.

As shown in Table 2, the multi-lipase immobilized preparation comprised of lipase PS and CALB exhibited improved synergistic transesterification activity in comparison with the control experiments, where FAME % reached 99.7%. The same synergistic trend was observed when lipase QLM was used in combination with lipases TL and PS.

Table 2 shows the percentage of the formed fatty acid methyl esters after 2, 3 and 6 hours of reaction time in transesterification system comprised of soybean oil triglycerides (220 g) and methanol (23.9 g) using different multi-lipase mixtures immobilized on Amberlite XAD 7HP, prepared according to Example 2 and also using immobilized lipases prepared according to Example 1 as control experiments. The reaction mixture was mechanically stirred at 30° C. for 6 hours.

TABLE 2

| Immobilized lipase on Amberlite XAD 7HP | FAME (%) After 2 hours | FAME (%) After 3 hours | FAME (%) After 6 hours |
|---|---|---|---|
| *Thermomyces lanuginose* lipase (control) | 75 | 82 | 85 |
| *Pseudomonas* sp. lipase (control) | 74 | 81 | 86 |
| *Candida antarctica* B lipase (control) | 10 | 18 | 42 |
| *Alcaligenes* sp. Lipase (Lipase QLM) | 52 | 67 | 88 |
| *Thermomyces lanuginosa* and *Candida antarctica* B lipases | 60 | 70 | 67 |
| *Pseudomonas* sp. and *Candida antarctica* B lipases | 82 | 96 | 99.7 |
| *Alcaligenes* sp. and *Thermomyces lanuginosa* Lipases | 71 | 78 | 96 |
| *Alcaligenes* sp. and *Pseudomonas* sp. Lipases | 86 | 98 | 99.5 |

Example 5

Figure 1:
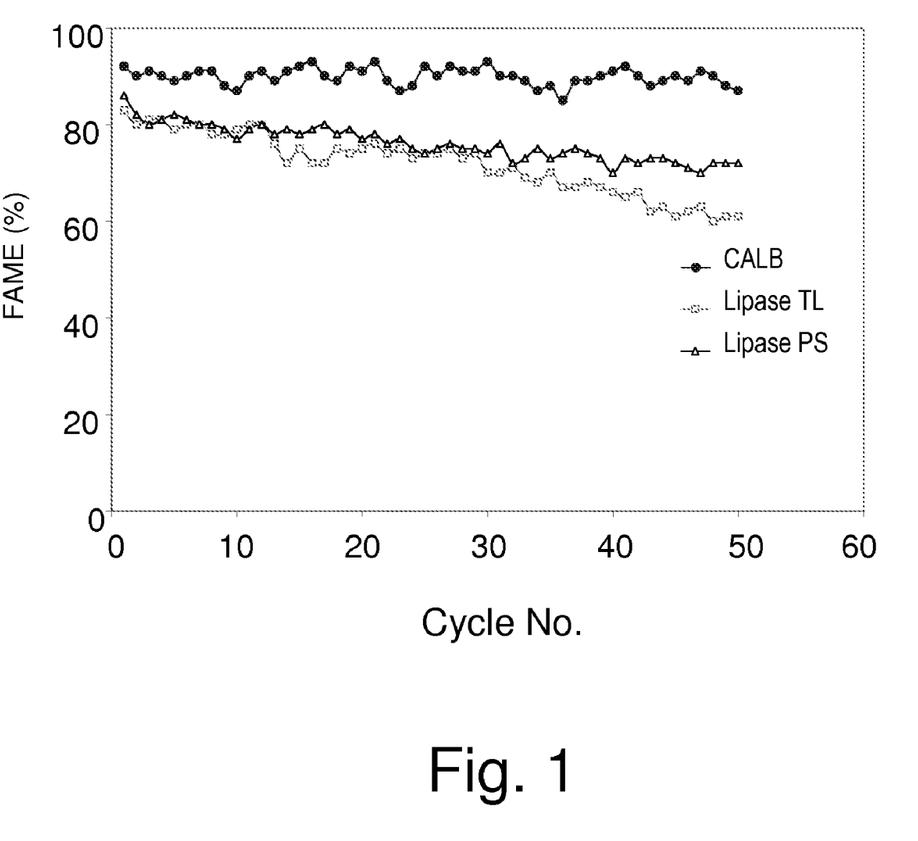
FIG. 1: The esterification activity of CALB, Lipase PS, Lipase TL, each immobilized separately on Amberlite XAD 7HP. Reaction conditions: oleic acid (2.5 g) and methanol (3 batches, each of 95 mg) were mixed with 250 mg immobilized lipase at 30° C. for 6 hours. The same batch of biocatalyst was used in 50 reaction cycles under the same conditions.

Repeated Esterification Activity of the Immobilized Lipases in Batch Reactions Using the Same Batch of Biocatalyst The esterification activity of the biocatalysts was tested by adding one of the three lipases (TL, SP, CALB) immobilized on Amberlite XAD 7HP (250 mg) into a screw-cap vial containing oleic acid (2.5 g) and ⅓ of the stoichiometric amount of methanol (285 mg). The remaining ⅔ of the amount of methanol were added in two equivalent batches, after 2 hours and after 4 hours of reaction time. The composition of the reaction mixture was analyzed after 6 hours. The reaction medium was discarded from the vial and a new batch of fresh substrates was introduced, using the same batch of enzyme. FIG. 1 shows the FAME % in the reaction medium, using the same batch of lipase PS, lipase TL or CALB, each separately immobilized on Amberlite XAD 7HP, in 50 reaction cycles.

The results presented in FIG. 1 show that immobilized CALB, lipases PS and TL preparations all efficiently catalyzed the esterification of free fatty acids and methanol. The repeated esterification activity of CALB was quite stable after 50 reaction cycles while the lipases TL and PS lost linearly 26% and 16% of the initial esterification activity after 50 reaction cycles, respectively.

Example 6

Repeated Transesterification Activity of the Immobilized Lipases in Batch Reactions Using the Same Batch of Biocatalyst The transesterification activity of the biocatalysts in repeated use was tested by adding one of the three lipases immobilized on Amberlite XAD 7HP (250 mg) into screw-cap vial containing soybeans oil (2.5 g) and ⅓ of the stoichiometric amount of methanol (91 mg). The remaining ⅔ of amount of methanol were added in two equivalent batches after 2 hours and after 4 hours of reaction time. The composition of the reaction mixture was analyzed after 6 hours. The reaction medium was discarded from the vial and a new batch of fresh substrates was introduced using the same batch of enzyme.

Figure 2:
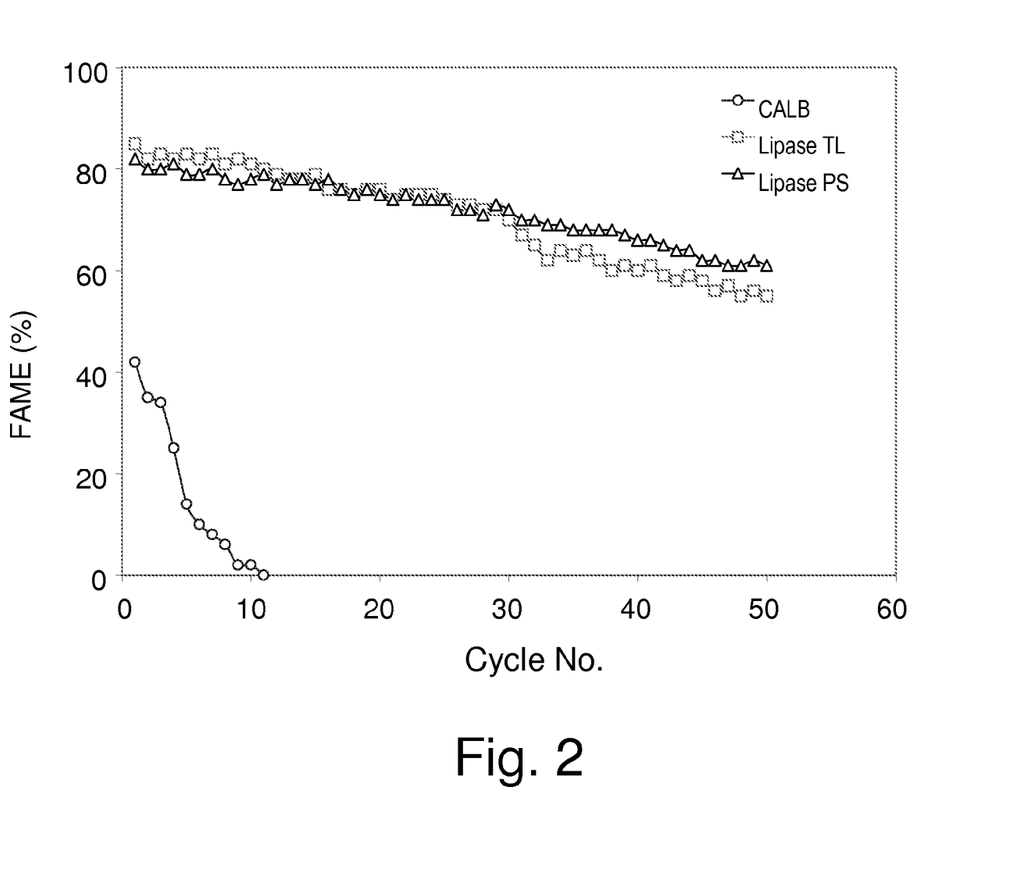
FIG. 2: The transesterification activity of CALB, Lipase PS, Lipase TL all immobilized separately on Amberlite XAD 7HP. Reaction conditions: Soybeans oil (2.5 g) and methanol (3 batches each 91 mg) were mixed with 250 mg immobilized lipase at 30° C. for 6 hours. The same batch of biocatalyst was used in 50 reaction cycles under the same conditions.

FIG. 2 shows the transesterification activity of the CALB, lipase PS and lipase TL, separately in 50 reaction cycles using the same batch of biocatalyst. The results show that the transesterification activity of both lipases PS and TL yielded FAME % below 85% and have decayed linearly and reached 70% in average of their initial transesterification activity after 50 reaction cycles. The initial transesterification activity of CALB was relatively low and unexpectedly lost its activity linearly after 11 reaction cycles.

Example 7

Use of Transesterification Activity-deficient CALB for Esterification Reactions of Fatty Acids and Alcohol CALB immobilized on Amberlite XAD 7HP which has lost its transesterification activity after 11 reaction cycles as described in Example 6 (25 omg) was used for the esterification of oleic acid (2.5 g) and methanol (285 mg). The same batch of biocatalyst was used in 10 reaction cycles. Unexpectedly, the analysis results show that the biocatalyst had a high esterification activity although it lost its transesterification activity in the former experiments. The average FAME % in 10 consecutive runs using the same batch of biocatalyst was 85%.

Example 8

Use of Transesterification Activity-deficient CALB for Tranesterification Reactions of Partial Glycerides and Alcohol CALB immobilized on Amberlite XAD 7HP which has lost its transesterification activity after 11 reaction cycles as described in Example 6 (250 mg) was used for the transesterification of monoolein (3 g) and methanol (270 mg). The same batch of biocatalyst was used in 10 reaction cycles. Unexpectedly, the analysis results show that the biocatalyst had a high transesterification activity for partial glycerides and methanol, although it lost its transesterification activity of triglycerides and methanol in the former experiments. The average FAME % in 10 consecutive runs using the same batch of biocatalyst was higher than 80%.

Example 9

Figure 3:
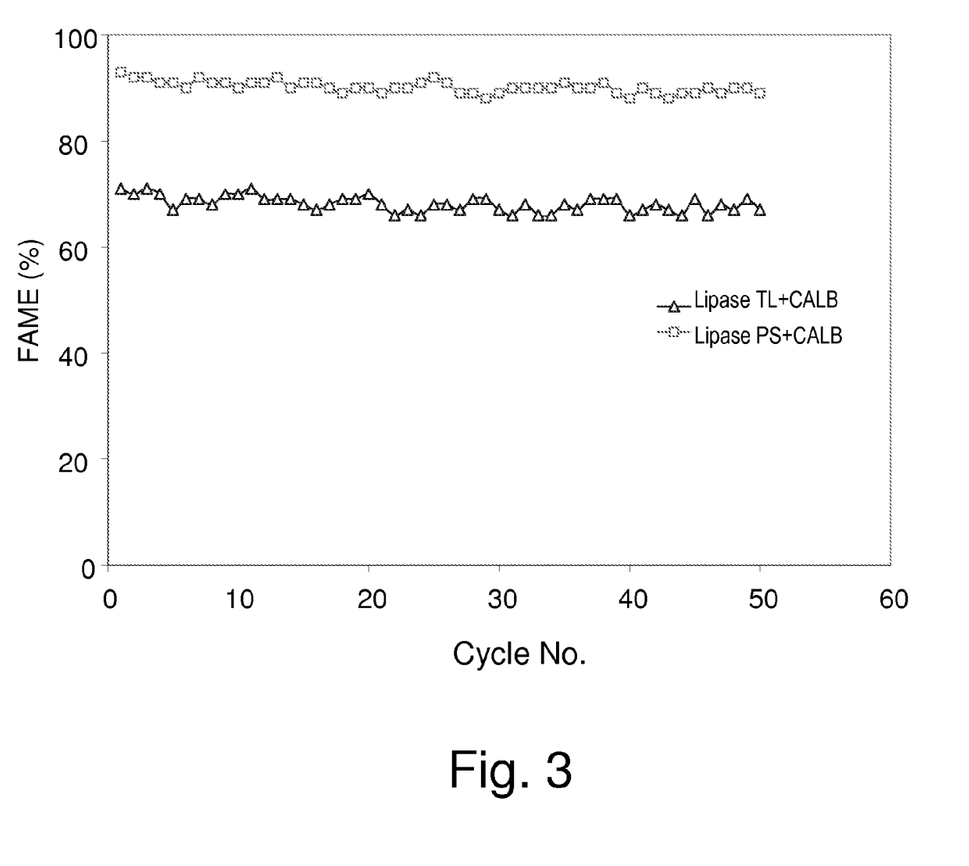
FIG. 3: The transesterification activity of multi-lipase immobilized on Amberlite XAD 7HP for either CALB and lipase TL or CALB and lipase PS. Reaction conditions: Soybeans oil (2.5 g) and methanol (3 batches each 91 mg) were mixed with 250 mg immobilized lipase at 30° C. for 6 hours. The same batch of biocatalyst was used in 50 reaction cycles under the same conditions.

Repeated Transesterification Activity of the Immobilized Multi-lipase Preparation in Batch Reactions Using the Same Batch of Biocatalyst The transesterification activity of the immobilized multi-lipase preparations were tested by adding either lipase PS and CALB or lipase TL and CALB all immobilized on Amberlite XAD 7HP (250 mg) according to example 1 or 2 into screw-cap vial containing soybeans oil (2.5 g) and $\frac{1}{3}$ of the stoichiometric amount of methanol (91 mg). The remaining $\frac{2}{3}$ of amount of methanol was added in two equivalent batches after 2 hours and after 4 hours of reaction time. The reaction medium was discarded from the vial after 6 hours of reaction and a new batch of fresh substrates was introduced using the same batch of enzyme. FIG. 3 shows the FAME % in the reaction medium using the same batch of biocatalyst in 50 cycles. The results presented in FIG. 3 show that the transesterification activity of both multi-lipase preparations are unexpectedly stable in 50 reaction cycles using the same batch of biocatalyst.

Example 10

Synthesis of Fatty Acid Methyl Esters (Biodiesel) Using Immobilized Multi-lipase Preparation in a Two-Step Process Table 3 shows the FAME % in transesterification reaction medium using multi-lipase preparation immobilized on Amberlite XAD 7HP comprised of either lipase TL and CALB, or lipase PS and CALB which were immobilized separately or in a one-pot system. Reactions were carried out by adding immobilized lipase preparation (30 g) to soybean oil (220 g) and methyl alcohol (23.9 g) into a double-jacketed glass reactor bottomed with a sintered glass filter of porosity of 70-100 μm. The methanol was added in batches each batch is $\frac{1}{3}$ of the stoichiometric amount or titrated drop-wise. The reaction system is mechanically stirred at 30° C. for 2 hours. When the substrate conversion reached preferably above 70% the reaction medium is filtered from the reactor bottom by applying nitrogen pressure or by its gravitational force over the sintered-glass filter. The reaction medium is either centrifuged or given some time to have phase separation. The bottom phase containing glycerol is removed and the organic phase containing the unreacted glycerides and FAME is introduced to a second consecutive bottomed sintered glass filter containing immobilized lipase. The medium in the second reactor is mechanically stirred with one third of the stoichiometric amount of the initially needed methanol for 2 hours at 30° C. The progress of the reaction was followed by measuring the percentage of fatty acid methyl esters, partial glycerides and triglycerides using GC after 2 hours.

The results presented in Table 3 show that both lipases TL and PS used as control experiments are capable to yield FAME % below 85% in the first step and 98% in the second step while CALB immobilized on Amberlite 7HP exhibited relatively low transesterification activity which did not exceed 15% after the two-step reaction. Mutli-lipase preparation comprised of lipase PS and CALB yielded 92% FAME in the first step and 100% in the second step. Unexpectedly, multi-lipase preparation comprised of lipase TL and CALB yielded relatively low FAME % of 70% and near to complete conversion in the second step. The low transesterification activity of the preparation of lipase TL and CALB in the first step can be attributed to the capability of such a complex biocatalyst to catalyze the reverse reaction of glycerol and fatty acid derivatives, while when glycerol was removed from the reaction medium the conversion to FAMAE % reached 99%. The combination of lipases TL and PS yielded high percentage of FAME in the first step and near to complete conversion at the second step.

Table 3 shows the percentage of the formed fatty acid methyl esters after 2 hours of reaction time for each step for the transesterification reaction system comprised of soybean oil triglycerides (220 g) and methanol (23.9 g) using different multi-lipase preparation immobilized on Amberlite XAD 7HP prepared according to Example 2. The reaction mixture was mechanically stirred at 30° C. for 2 hours. After phase separation, the upper organic phase was introduced to a second reactor containing immobilized lipase which operates under the same reaction conditions.

TABLE 3

| Step No. | Lipase PS FAME (%) | Lipase TL FAME (%) | CALB FAME (%) | PS/CALB FAME (%) | TL/CALB FAME (%) | PS/TL FAME (%) |
|---|---|---|---|---|---|---|
| Step 1 | 80 | 85 | 5 | 92 | 70 | 85 |
| Step 2 | 98 | 98 | 15 | 100 | 99 | 99 |

Figure 4:
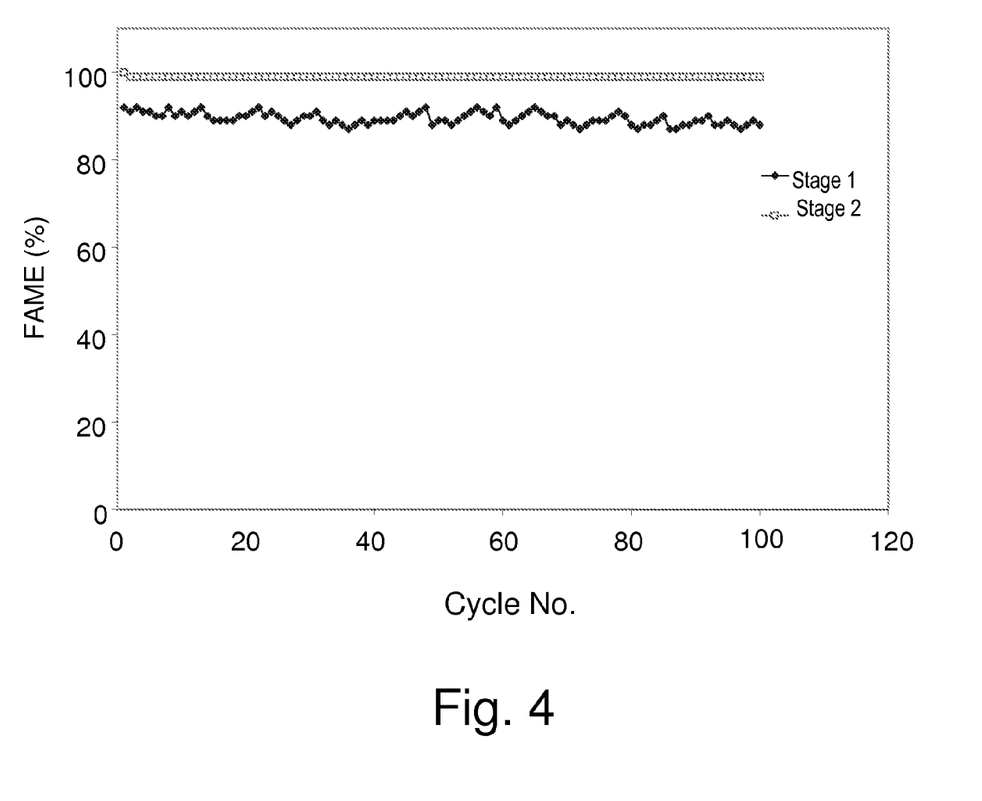
FIG. 4: FAME % in the two-stage transesterification process using lipase PS and CALB both immobilized on Amberlite XAD 7HP. Reaction conditions: The reaction was initiated by adding biocatalyst (30 g) to soybean oil (220 g) and methyl alcohol (23.9 g) into a double-jacketed glass reactor bottomed with a sintered glass filter of porosity of 70-100 μm. The methanol was added in batches each batch is ⅓ of the stoichiometric amount or titrated drop-wise. The reaction system is mechanically stirred at 30° C. for 2 hours. The reaction medium was removed from the first stage, centrifuged to remove glycerol and then introduced to the second-stage reactor and stirred for two hours.

Table 3 shows various possibilities for different synergistic enzyme combinations (as can be seen in FIGS. 3 and 4 where multi-enzyme systems were used compared to FIG. 2 where one enzyme was used).

The reaction time is shortened down to 2-3 hours, due to the presence of CALB, responsible for the clearance of the intermediate partial glycerides, namely mono- and diglycerides, in addition to the clearance of the formed glycerol typically responsible for prolongation of the reaction time and deactivation of the enzyme when only lipase PS or lipase TL are used separately.

Example 11

Synthesis of Fatty Acid Methyl Esters (Biodiesel) Using Immobilized Multi-lipase Preparation in a Two-step Process Using the Same Biocatalyst in Consecutive Batches FIG. 4 shows FAME % in stages 1 and 2 for transesterification reaction medium using multi-lipase preparation immobilized on Amberlite XAD 7HP comprised of lipase PS and CALB which were immobilized separately or in one-pot system. Reactions were carried out by adding biocatalyst (30 g) to soybean oil (220 g) and methyl alcohol (23.9 g) into a double-jacketed glass reactor bottomed with a sintered glass filter of porosity of 70-100 μm. The methanol was added in batches each batch is ⅓ of the stoichiometric amount or titrated drop-wise. The reaction system is mechanically stirred at 30° C. for 2 hours. When the substrate conversion reaches preferably above 80% the reaction medium is filtered by nitrogen pressure or by its gravitational force over the sintered-glass filter. The reaction medium is either centrifuged or given some time to have phase separation. The bottom phase containing glycerol was removed and the organic phase containing the unreacted glycerides and FAME is introduced to a second consecutive bottomed sintered glass filter containing the same biocatalyst. The medium in the second reactor is mechanically stirred with one third of the stoichiometric amount of the initially needed methanol for 2 hours at 30° C. The reaction medium is removed from the reactor maintaining the same biocatalyst. This procedure was repeated at least 100 cycles. FIG. 4 shows the FAME % after 2 hours of reaction time in each cycle in the two-stage process. The results in FIG. 4 show that the percentage of FAME after the first stage was approximately 88% in average and reached above 99% in average after the second step. Unexpectedly, the results show that the multi-lipase immobilized preparation is highly active and no significant activity losses were observed in 100 reaction cycles using the same batch of biocatalyst.

The invention claimed is:

1. A process for the preparation of short-chain alkyl esters of fatty acids in solvent-free system comprising:
providing a fatty acid source, stepwise adding a short-chain free alcohol or any other alcohol donor, to said fatty acid source in the presence of a lipase preparation and allowing the reaction to proceed under suitable conditions, until said fatty acid source triglycerides are converted to fatty acid alkyl esters, wherein said lipase preparation comprises at least two lipases, said lipases being separately or jointly immobilized on a suitable support and wherein at least one of said lipases has increased affinity for partial glycerides is derived from any one of *Candida antarctica* B, *Alcaligenes* sp. and *Penicillium camembertii* and at least one of said lipases is sn-1,3 positional specific and is derived from any one of *Thermomyces lanuginose, Rhizomucor miehei, Mucor javanicus, Pseudomonas* sp., *Penicillium roqueforti, Aspergillus niger, Acromobacter* sp. and *Burkholderia* sp.

2. The process of claim 1, wherein said fatty acid source comprises at least one of soybean oil, canola oil, rapeseed oil, olive oil, castor oil, palm oil, sunflower oil, peanut oil, cotton seed oil, Jatropha oil, animal-derived fat, waste cooking oil, oil triglycerides derived from inedible plant sources, or any mixture of at least two thereof.

3. The process of claim 1, wherein said lipases are jointly immobilized on a suitable support.

4. The process of claim 1, wherein each of said lipases is immobilized on a suitable support, and wherein the supports on which the said lipases are immobilized are identical or different.

5. The process of claim 1, wherein said support is a porous support which is organic or inorganic wherein said inorganic porous support is silica-based or alumina-based, and said organic porous support is polymer-based, and wherein said support may optionally contain active functional groups selected from epoxy and aldehyde groups, or ionic groups.

6. The process of claim 1, wherein the conversion of the fatty acid acyl groups or free fatty acids comprised in said fatty acid source to fatty acid alkyl esters is monitored at various time points during the reaction, the reaction medium is removed by suitable means at any desired time point during the reaction, thereby stopping the reaction, and the formed fatty acid alkyl esters and optionally the formed glycerol are isolated from the reaction medium.

7. The process of claim 6, wherein the reaction is stopped when the conversion of the fatty acid acyl groups or free fatty acids comprised in said fatty acid source to fatty acid alkyl esters has reached at least 70%.

8. A solvent-free process for the preparation of short-chain alkyl esters of fatty acids comprising:
providing a fatty acid source, stepwise adding a short-chain free alcohol or any other alcohol donor, to said fatty acid source in the presence of a lipase preparation and allowing the reaction to proceed under suitable conditions, until the conversion of the fatty acid acyl groups or free fatty acids comprised in said fatty acid source to fatty acid alkyl esters reaches at least 70% wherein said lipase preparation comprises a single one lipase immobilized on a suitable support, said single lipase being derived from any one of *Candida antarctica* B, *Alcaligenes* sp., *Penicillium camembertii, Thermomyces lanuginose, Rhizomucor miehei, Mucor javanicus, Pseudomonas* sp., *Penicillium roquefortii, Aspergillus niger, Acromobacter* sp. and *Burkholderia* sp., or said lipase preparation comprises a mixture of at least two lipases jointly or separately immobilized on a suitable support, wherein at least one of said two lipases has increased affinity for partial glycerides and is derived from any one of *Candida antarctica* B, *Alcaligenes* sp. and *Penicillium camembertii* and at least one of said lipases is sn-1,3 positional specific and is derived from any one of *Thermomyces lanuginose, Rhizomucor miehei, Mucor*

*javanicus*, *Pseudomonas* sp., *Penicillium roqueforti*, *Aspergillus niger*, *Acromobacter* sp. and *Burkholderia* sp., while continuously removing the formed glycerol and any excess water from the reaction mixture.

9. The process of claim 8, wherein said lipase preparation comprises at least two lipases, said lipases being separately or jointly immobilized on a suitable support.

10. The process of claim 8, wherein said fatty acid source comprises at least one of soybean oil, canola oil, rapeseed oil, olive oil, castor oil, palm oil, sunflower oil, peanut oil, cotton seed oil, Jatropha oil, animal-derived fat, waste cooking oil, oil triglycerides derived from inedible plant sources, or any mixture of at least two thereof.

11. The process of claim 8, wherein said lipases are jointly immobilized on a suitable support.

12. The process of claim 8, wherein each of said lipases is immobilized on a suitable support, and wherein the supports on which the said lipases are immobilized are identical or different.

13. The process of claim 8, wherein said support is a porous support which is organic or inorganic wherein said inorganic porous support is silica-based or alumina-based, and said organic porous support is polymer-based, and wherein said support may optionally contain active functional groups selected from epoxy and aldehyde groups, or ionic groups.

14. The process of claim 8, wherein the conversion of the fatty acid acyl groups or free fatty acids comprised in said fatty acid source to fatty acid alkyl esters is monitored at various time points during the reaction, the reaction medium is removed by suitable means at any desired time point during the reaction, thereby stopping the reaction, and the formed fatty acid alkyl esters and optionally the formed glycerol are isolated from the reaction medium.

15. The process of claim 14, wherein the reaction is stopped when the conversion of the fatty acid acyl groups or free fatty acids comprised in said fatty acid source to fatty acid alkyl esters has reached at least 70%.

16. A solvent-free process for the preparation of short-chain free alkyl esters of fatty acids comprising:
   (a) providing a fatty acid source, stepwise adding a short-chain alcohol or any other alcohol donor, to said fatty acid source in the presence of a lipase preparation and allowing the reaction to proceed under suitable conditions, until the conversion of the fatty acid acyl groups or free fatty acids comprised in said fatty acid source to fatty acid alkyl esters reaches at least 70% wherein said lipase preparation comprises at least one lipase immobilized on a suitable support, said single lipase being derived from any one of *Candida antarctica* B, *Alcaligenes* sp., *Penicillium camembertii*, *Thermomyces lanuginose*, *Rhizomucor miehei*, *Mucor javanicus*, *Pseudomonas* sp., *Penicillium roqueforti*, *Aspergillus niger*, *Acromobacter* sp. and *Burkholderia* sp., or said lipase preparation comprises a mixture of at least two lipases jointly or separately immobilized on a suitable support, wherein at least one of said two lipases has increased affinity for partial glycerides and is derived from any one of *Candida antarctica* B, *Alcaligenes* sp. and *Penicillium camembertii* and at least one of said lipases is sn-1,3 positional specific and is derived from any one of *Thermomyces lanuginose*, *Rhizomucor miehei*, *Mucor javanicus*, *Pseudomonas* sp., *Penicillium roqueforti*, *Aspergillus niger*, *Acromobacter* sp. and *Burkholderia* sp., while continuously removing the formed glycerol from the reaction mixture, to yield an organic phase containing mainly residual un-reacted glycerides and the formed fatty acid alkyl esters; and
   (b) reacting the said organic phase with a short-chain free alcohol or any other alcohol donor, in the presence of a lipase preparation as defined in step (a) under suitable conditions, until the conversion of the fatty acid acyl groups or free fatty acids comprised in said fatty acid source to fatty acid alkyl esters reaches at least 95%.

17. The process of claim 16, wherein said lipases are jointly immobilized on a suitable support.

18. The process of claim 16, wherein each of said at least one lipase is separately immobilized on a suitable support, and wherein the supports on which the said lipases are immobilized are identical or different.

19. The process of claim 16, wherein said support is a porous support which is organic or inorganic wherein said inorganic porous support is silica-based or alumina-based, and said organic porous support is polymer-based, and wherein said support may optionally contain active functional groups selected from epoxy and aldehyde groups, or ionic groups.

20. The process of claim 16, wherein said fatty acid source comprises at least one of soybean oil, canola oil, rapeseed oil, olive oil, castor oil, palm oil, sunflower oil, peanut oil, cotton seed oil, Jatropha oil, animal-derived fat, waste cooking oil, oil triglycerides derived from inedible plant sources, or any mixture of at least two thereof.

21. A process for the preparation of a mixture of lipases immobilized on an insoluble support, said mixture comprising a lipase derived from *Candida antarctica* B and at least one lipase derived from *Pseudomonas* sp., *Alcaligenes* sp., *Burkholderia* sp., and *Thermomyces lanuginosa*, the process comprising the steps of:
   (a) contacting a buffer solution containing a lipase derived from *Candida Antarctica* B and at least one lipase derived from *Pseudomonas* sp., *Alcaligenes* sp., *Burkholderia* sp., and *Thermomyces lanuginosa* with a polymeric matrix which may be any one of an ion exchange resin or an adsorbent; in the presence of a hydrophobic organic solvent, added to the immobilization medium at ratios of 1:10 to 10:1 buffer:organic solvent, respectively;
   (b) mixing the system obtained in step (a) for at least 4 hours at room temperature,
   (c) filtering off of the immobilized lipase mixture, and drying it to a water content of less than 5%.

22. The process of claim 21, wherein said insoluble support is Amberlite XAD-1600 or Amberlite 7HP.

23. A process for the preparation of biodiesel employing the immobilized lipase mixture prepared by the process of claim 21.

24. A process for the preparation of biodiesel employing the immobilized lipase mixture prepared by the process of claim 22.

25. The process of claim 1, wherein said short-chain free alcohol is methanol and said short-chain fatty acid alkyl esters are fatty acid methyl esters (biodiesel).

26. The process of claim 8, wherein said short-chain free alcohol is methanol and said short-chain fatty acid alkyl esters are fatty acid methyl esters (biodiesel).

27. The process of claim 16, wherein said short-chain free alcohol is methanol and said short-chain fatty acid alkyl esters are fatty acid methyl esters (biodiesel).

28. The process of claim 7, wherein the reaction is stopped when the conversion of the fatty acid acyl groups or free fatty acids comprised in said fatty acid source to fatty acid methyl esters has reached at least 85%.

29. The process of claim 15, wherein the reaction is stopped when the conversion of the fatty acid acyl groups or free fatty acids comprised in said fatty acid source to fatty acid methyl esters has reached at least 85%.

30. The process of claim 21, wherein said solvent is n-hexane.

31. The process of claim 7, wherein the reaction is stopped when the conversion of the fatty acid acyl groups or free fatty acids comprised in said fatty acid source to fatty acid methyl esters has reached at least 95%.

32. The process of claim 15, wherein the reaction is stopped when the conversion of the fatty acid acyl groups or free fatty acids comprised in said fatty acid source to fatty acid methyl esters has reached at least 95%.

* * * * *